(12) United States Patent
El-Beltagi et al.

(10) Patent No.: US 12,006,272 B1
(45) Date of Patent: Jun. 11, 2024

(54) NITROGEN ACTIVATOR STABILIZER FOR REDUCING AND PROTECTING NITROGEN FERTILIZER

(71) Applicant: KING FAISAL UNIVERSITY, Al-Ahsa (SA)

(72) Inventors: Hossam El-Din Saad El-Beltagi, Al-Ahsa (SA); Khaled Mohamed Amen Ramadan, Al-Ahsa (SA); Hani Saber Sayed Saudy, Al-Ahsa (SA); Sameh Ahmed Rizk, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/425,949

(22) Filed: Jan. 29, 2024

Related U.S. Application Data

(60) Continuation-in-part of application No. 18/230,985, filed on Aug. 7, 2023, now abandoned, which is a division of application No. 18/144,332, filed on May 8, 2023.

(51) Int. Cl.
| | |
|---|---|
| *A01C 21/00* | (2006.01) |
| *C05B 7/00* | (2006.01) |
| *C05C 9/00* | (2006.01) |
| *C05G 1/00* | (2006.01) |
| *C05G 3/40* | (2020.01) |
| *C05G 5/18* | (2020.01) |
| *C05G 5/30* | (2020.01) |
| *C07D 473/30* | (2006.01) |

(52) U.S. Cl.
CPC ............... *C05G 3/44* (2020.02); *A01C 21/00* (2013.01); *C05B 7/00* (2013.01); *C05C 9/005* (2013.01); *C05G 1/00* (2013.01); *C05G 5/18* (2020.02); *C05G 5/38* (2020.02); *C07D 473/30* (2013.01)

(58) Field of Classification Search
CPC ... C05G 3/44; C05G 1/00; C05G 5/18; C05G 5/38; A01C 21/00; C05B 7/00; C05C 9/005; C07D 473/30
See application file for complete search history.

(56) References Cited

U.S. PATENT DOCUMENTS

| | | |
|---|---|---|
| 2019/0359534 A1 | 11/2019 | Zhang et al. |
| 2021/0292252 A1 | 9/2021 | Thompson et al. |
| 2021/0363073 A1 | 11/2021 | Nguyen et al. |
| 2021/0387925 A1 | 12/2021 | Saettone et al. |

OTHER PUBLICATIONS

Vejan, et al.; "Controlled release fertilizer: A review on developments, applications and potential in agriculture", Journal of Controlled Release vol. 339, Nov. 10, 2021, pp. 321-334.

(Continued)

*Primary Examiner* — Jennifer A Smith
(74) *Attorney, Agent, or Firm* — Nath, Goldberg & Meyer; Richard C. Litman

(57) ABSTRACT

A nitrogen activator additive to stabilize nitrogen fertilizer, where the activator is coated onto the nitrogen fertilizer, is provided. The nitrogen activator additive contains the novel compound ABT-PNB, a potassium compound, and chitosan, and provides controlled release of the nitrogen fertilizer which fertilizes crops using reduced levels of the nitrogen fertilizer and reduces the release of greenhouse gasses. Urea is an exemplary nitrogen fertilizer that can be used in this regard.

18 Claims, 6 Drawing Sheets

(56) References Cited

OTHER PUBLICATIONS

Elshayb, et al.; "Utilizing Urea-Chitosan Nanohybrid for Minimizing Synthetic Urea Application and Maximizing *Oryza sativa* L. Productivity and N Uptake", Agriculture 2022, 12(7), 944; https://doi.org/10.3390/agriculture12070944 Received: May 17, 2022 / Revised: Jun. 22, 2022 / Accepted: Jun. 24, 2022 / Published: Jun. 29, 2022.

NITROGEN ACTIVATOR STABILIZER FOR REDUCING AND PROTECTING NITROGEN FERTILIZER

CROSS-REFERENCE TO RELATED APPLICATION

This application is a continuation-in-part (CIP) of U.S. patent application Ser. No. 18/230,985, filed on Aug. 7, 2023, which application is a divisional of U.S. patent application Ser. No. 18/144,332, filed on May 8, 2023, the entire contents of which is hereby incorporated by reference.

BACKGROUND

1. Field

The disclosure of the present patent application relates to a nitrogen activator to stabilize nitrogen fertilizer and control its release, where the activator is coated onto the nitrogen fertilizer.

2. Description of the Related Art

Due to current climate change challenges, there are concerns as to the sustainable development of the world, particularly in terms of greenhouse gas production. It is known that the global increase in energy usage alone contributes to 80% of all greenhouse gases (GHG) due to increased consumption of fossil fuels and the use of excess fertilizer to meet sandy soil demands. For example, wheat Fadden requires 60-70 kg of seeds and around 300 kg nitrogen, potassium, and super phosphate fertilizer to produce 1.8 ton of wheat when using well water having a degree of salinity of 2400-2550 ppm and clay soil having a salinity of 3700-3800 ppm under normal conditions.

To date, efforts in this field have focused on controlled release fertilizer (CRF). The application of CRF has been effective as an environmentally sustainable pathway to increase crop yields by allowing desired plant growth via a direct or indirect mechanism. The mechanism of CRF not only decreases nutrient dissipation due to volatilization and leaching, but also provides a precisely appropriate nutrient release design that is suitable in the physiological and biochemical aspect of the plant growth. However, CRF is not deployed on larger scale of commercial agriculture practices due to it being expensive, having relatively low efficiency in releasing nutrients, and the coatings being largely composed of petroleum-based synthetic polymers. Further, conventional production of slow-release nitrogen compounds can have complicated production processes and can be energy intensive.

Thus, a controlled release fertilizer that reduces nitrogen fertilizer usage and production of greenhouse gases, maintains current CRF advantages, and mitigates or eliminates the above problems, is desired.

SUMMARY

The presently disclosed subject matter relates to a nitrogen activator stabilized fertilizer (NASF1). This stabilized fertilizer can be used in, for example, mass production of wheat and corn. The activator is coated onto nitrogen fertilizer particles and can cause controlled and sustained release of the fertilizer, thus preserving the nitrogen release and affording efficient green technology for wheat Fadden production, for example, particularly under conditions of salinity stress. NASF1 may be used to assist in irrigation of agricultural soil lands at a reasonable cost and reduce the amount of fertilizer used. The NASF1 product (coated fertilizer) not only can increase yields of, for example, wheat and corn mass production, but can also promote sustainable environmental land use with decreased greenhouse gas emissions (e.g., $N_2$, $CO_2$, etc.), while saving time and energy.

The NASF1 product can comprise a coating of the nitrogen containing fertilizer, wherein the coating can include the novel compound 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB) along with potassium phosphate, and chitosan, each in specific amounts. In further embodiments, the nitrogen fertilizer particles to which the coating is applied can comprise urea as the nitrogen fertilizer.

In an embodiment, the presently disclosed subject matter relates to a nitrogen activator additive to stabilize nitrogen fertilizer, wherein the activator is coated onto the fertilizer to reduce the use and release of and protect the nitrogen fertilizer. Further contemplated herein is an NASF1 product comprising an activator-coated fertilizer particle, as well as processes for synthesizing and using said nitrogen activator additive.

Accordingly, in one embodiment, the present subject matter relates to a stabilized nitrogen activator additive fertilizer (NASF1) composition to stabilize nitrogen fertilizer, the composition comprising a potassium compound, chitosan, urea, and 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB), with the ABT-PNB having the following structure:

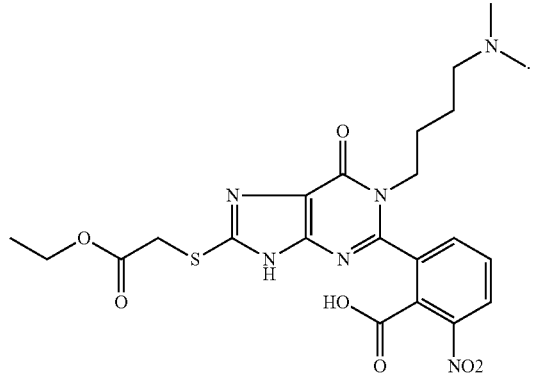

In other embodiments, the NASF1 composition may include various amounts of each chemical component. In certain embodiments, the potassium compound can be selected from the group consisting of potassium phosphate, potassium nitrate, potassium tartrate, and combinations thereof.

In an embodiment, the present subject matter relates to a nitrogen activator stabilizer fertilizer (NASF1) composition, the composition comprising a coated slow-release fertilizer composition comprising: a core comprising a nitrogen-based fertilizer; and at least one coating layer surrounding the core, wherein the at least one coating layer comprise a potassium compound, chitosan, and 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB), with the ABT-PNB having the following structure:

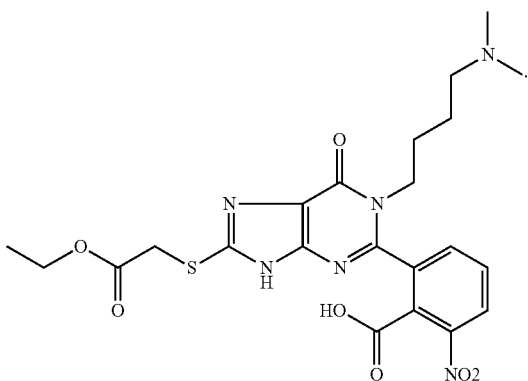

In another embodiment, the present subject matter relates to a method for synthesizing the NASF1.

In an embodiment, present subject matter relates to a method for using the NASF1 additive-coated fertilizer for agricultural crop improvements. In this regard, the present subject matter relates to a method of fertilizing crops, comprising applying the compositions as described herein to said crops.

These and other features of the present subject matter will become readily apparent upon further review of the following specification.

DETAILED DESCRIPTION OF THE PREFERRED EMBODIMENTS

Figure 1:
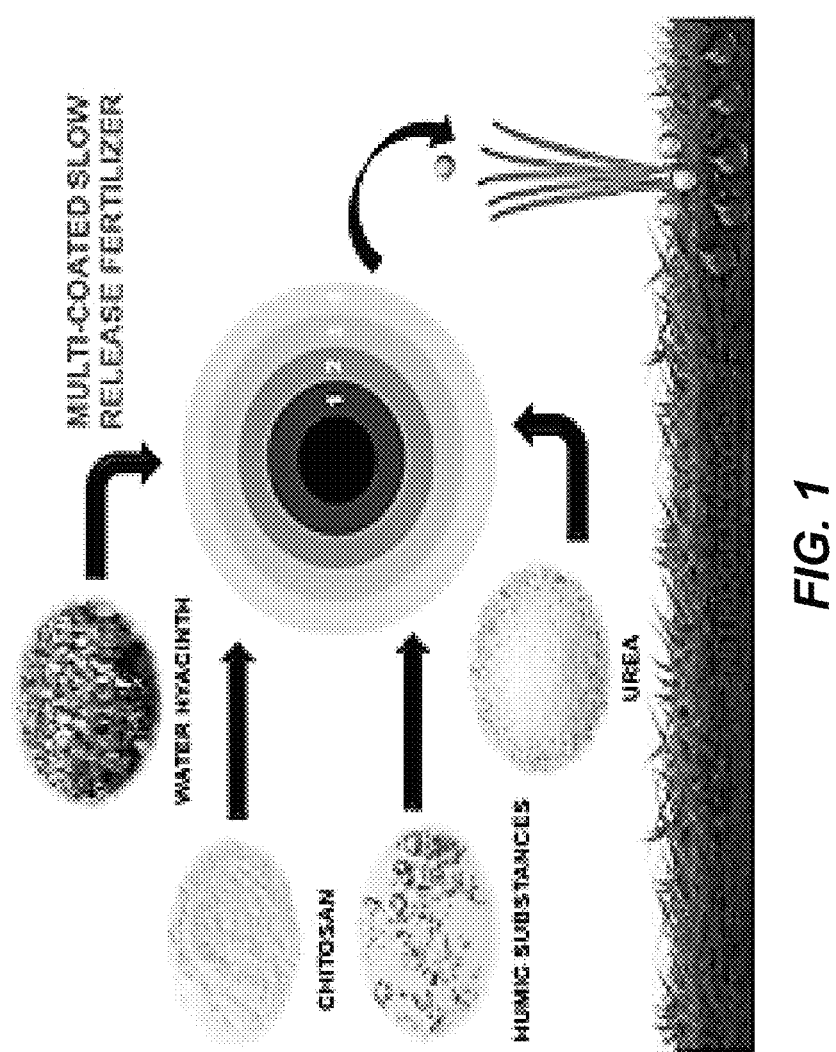
FIG. 1 shows a multi-coated fertilizer particle as described herein.
Figure 2:
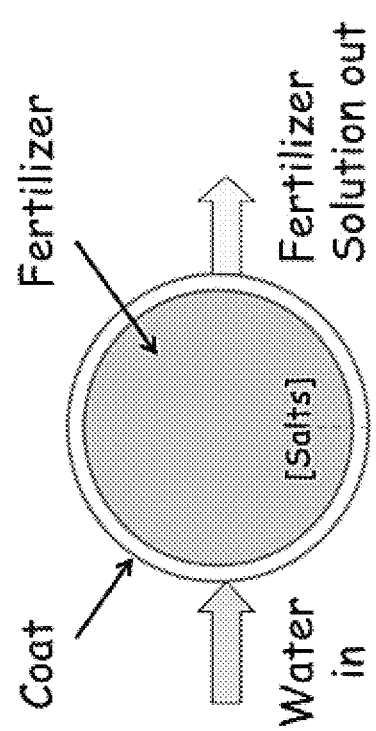
FIG. 2 shows the effect of applying water to the present NASF1 compositions.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The presently disclosed subject matter relates to a nitrogen activator stabilized fertilizer (NASF1). This stabilized fertilizer can be used in, for example, mass production of wheat and corn. The activator is coated onto nitrogen fertilizer particles and can cause controlled and sustained release of the fertilizer, thus preserving the nitrogen release and affording efficient green technology for wheat Fadden production, for example, particularly under conditions of salinity stress. NASF1 may be used to assist in irrigation of agricultural soil lands at a reasonable cost and reduce the amount of fertilizer used. The NASF1 product (coated fertilizer) not only can increase yields of, for example, wheat and corn mass production, but can also promote sustainable environmental land use with decreased greenhouse gas emissions (e.g., $N_2$, $CO_2$, etc.), while saving time and energy.

The NASF1 product can comprise a coating of the nitrogen containing fertilizer, wherein the coating can include the novel compound 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB) along with potassium phosphate, and chitosan, each in specific amounts. In further embodiments, the nitrogen fertilizer particles to which the coating is applied can comprise urea as the nitrogen fertilizer.

In an embodiment, the presently disclosed subject matter relates to a nitrogen activator additive to stabilize nitrogen fertilizer, wherein the activator is coated onto the fertilizer to reduce the use and release of and protect the nitrogen fertilizer. Further contemplated herein is an NASF1 product comprising an activator-coated fertilizer particle, as well as processes for synthesizing and using said nitrogen activator additive.

Accordingly, in one embodiment, the present subject matter relates to a stabilized nitrogen activator additive fertilizer (NASF1) composition to stabilize nitrogen fertilizer, the composition comprising a potassium compound, chitosan, urea, and 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB), with the ABT-PNB having the following structure:

Accordingly, in one embodiment, the present subject matter relates to the compound 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB), with the ABT-PNB having the following structure:

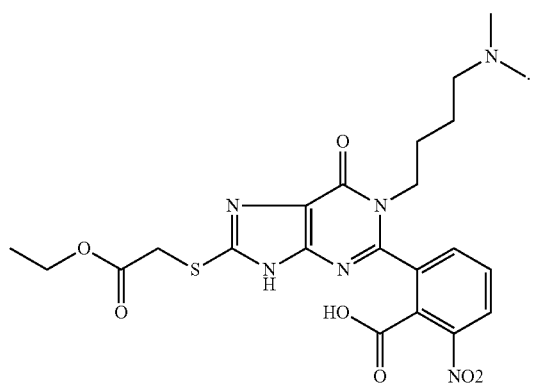

Figure 4:
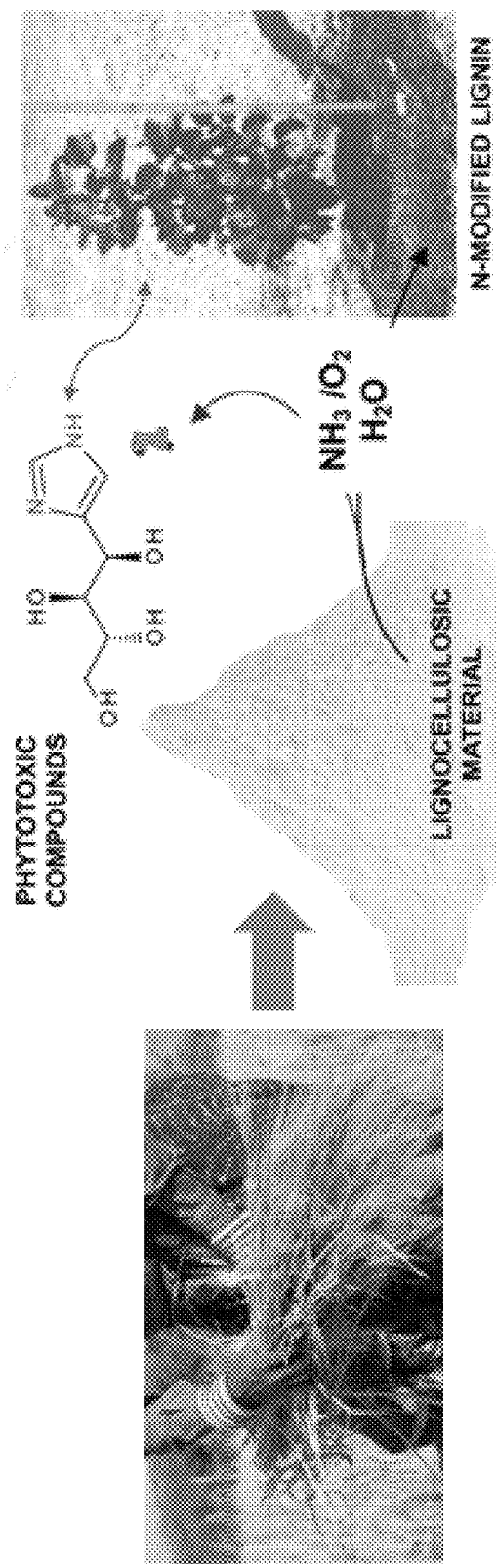
FIG. 4 shows a schematic representation of lignocellulosic material extraction.
Figure 5:
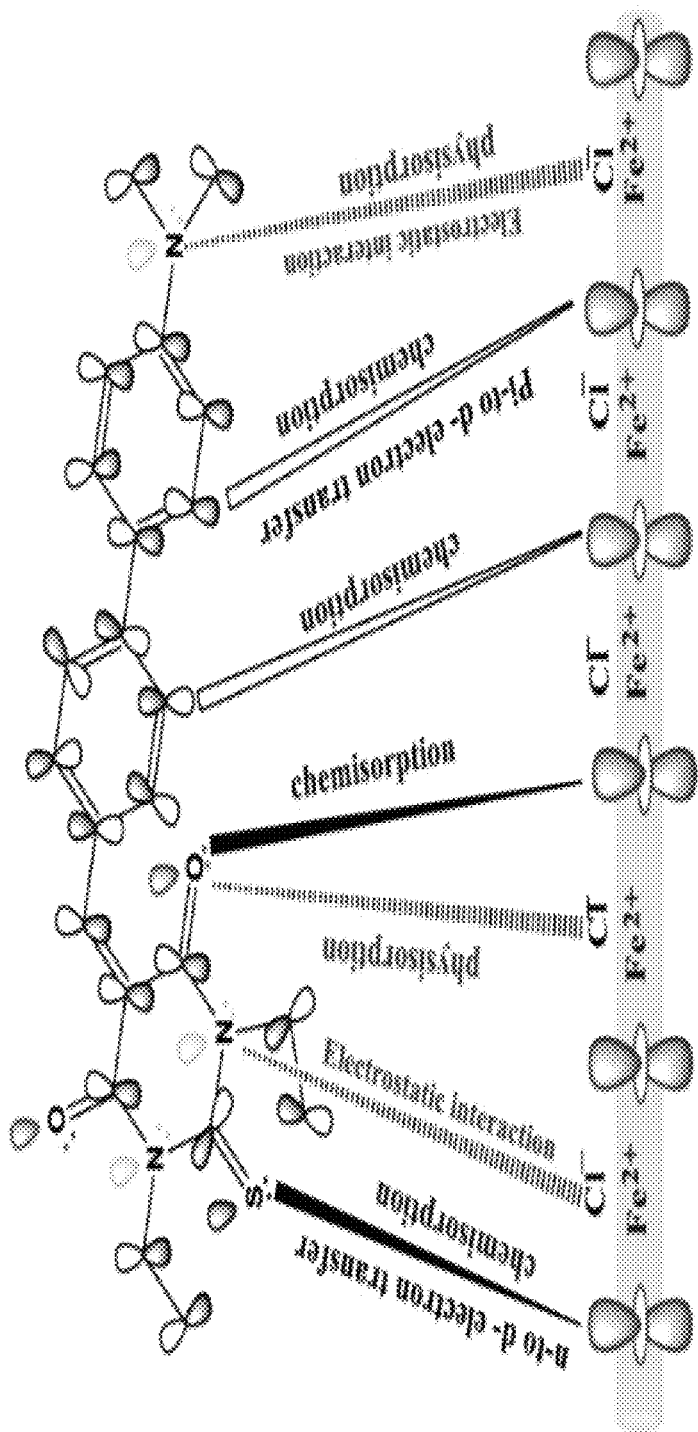
FIG. 5 depicts the physico- and chemi-sorption of Fe with pyrimidine to obtain NASF1.

In this regard, the ABT-PNB compound can be the result of an efficient and sustainable procedure for agricultural straw waste to afford β-O-4 lignocellulosic reproductions as shown in FIG. 4 via microwave-ultrasonic reaction conditions as described herein. Microwave-ultrasonic assisted for Lignin extract to access some heterocyclic precursors, e.g., pyrimidine, purine, pyridine, imidazole, pyrazole, and quinazoline moieties. The ultrasonic-assisted-microwave provides significantly speedy synthesis with reduced time. One-pot synthesis of pyrimidine derivatives to create nitrogen fertilizer agents, e.g., the ABT-PNB compound and for using iron nanoparticles FeNPs with pyrimidine compound to afford NASF1 as another type of nitrogen activators is shown in FIG. 5.

In one embodiment, a retro synthetic analysis for the ABT-PNB compound can be seen according to the following Scheme 1:

Scheme 1

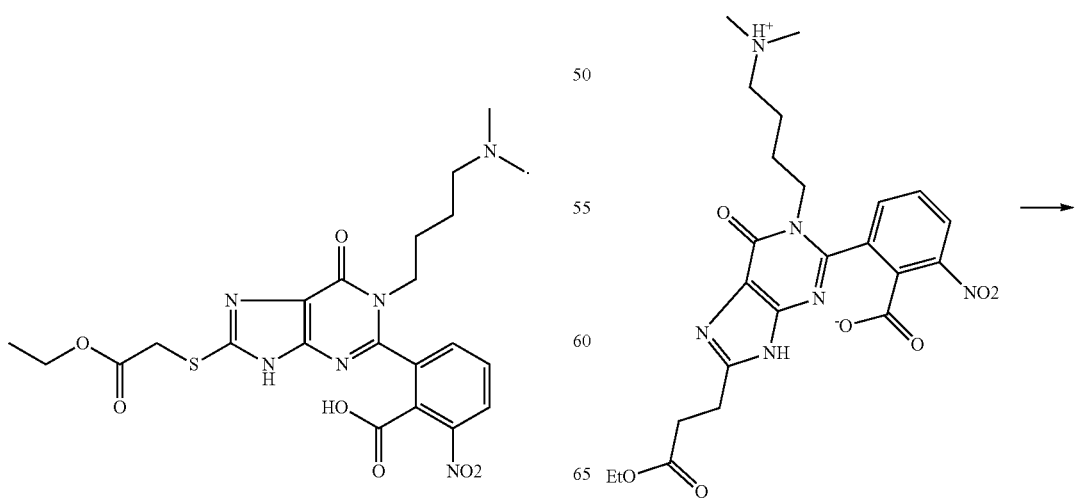

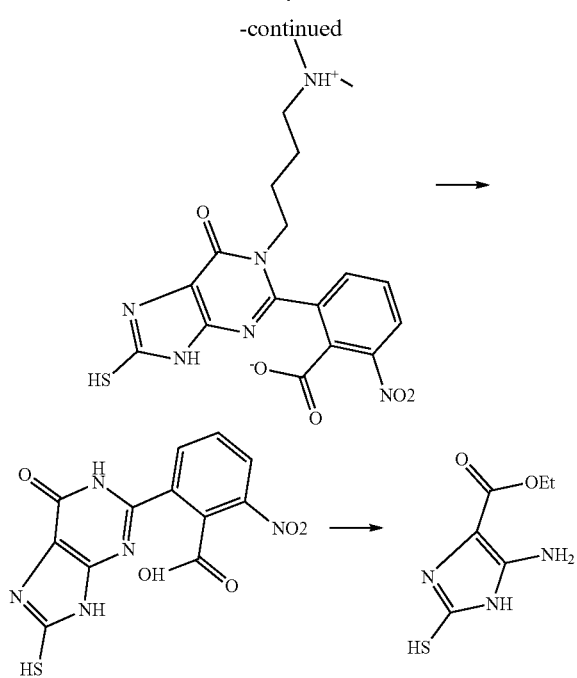

In another embodiment, certain synthetic routes for obtaining the ABT-PNB compound can be seen according to the following Scheme 2:

The retrosynthetic analysis shown in Scheme 1 can assist in the synthesis of the target (ABT-PNB) as per Scheme 2. Specifically, reaction of ethyl 5-amino-2-mercapto-1H-imidazole-4-carboxylate (1) with 2-cyano-6-nitrobenzoic acid (2) affords 2-(8-mercapto-6-oxo-6,9-dihydro-1H-purin-2-yl)-6-nitrobenzoic acid (3) via microwave-ultrasonic reaction condition for 10 min. DFT stimulation can confirm the electrophilicity of the cyano group that has been more than the carboxylic group in the compound 2, allowing the promotion of the compound 3. Reaction of the compound 3 with ethylchloroacetate affords 2-(8-((2-ethoxy-2-oxoethyl)thio)-6-oxo-6,9-dihydro-1H-purin-2-yl)-6-nitrobenzoic acid (4). Reaction of the compound 4 with 4-chloro-N,N-dimethylbutan-1-amine affords the nitrogen activator fertilizer target, ABT-PNB.

In an embodiment, the present subject matter relates to a nitrogen activator stabilizer fertilizer (NASF1) composition, the composition comprising a coated slow-release fertilizer composition comprising: a core comprising a nitrogen-based fertilizer; and at least one coating layer surrounding the core, wherein the at least one coating layer comprises a potassium compound, chitosan, and 2-(1-(4-(dimethylamino)butyl)-8-((2-ethoxy-2-oxoethyl)thio)-6-oxo-6,9-dihydro-1H-purin-2-yl)-6-nitrobenzoic acid (ABT-PNB), with the ABT-PNB having the following structure:

Scheme 2

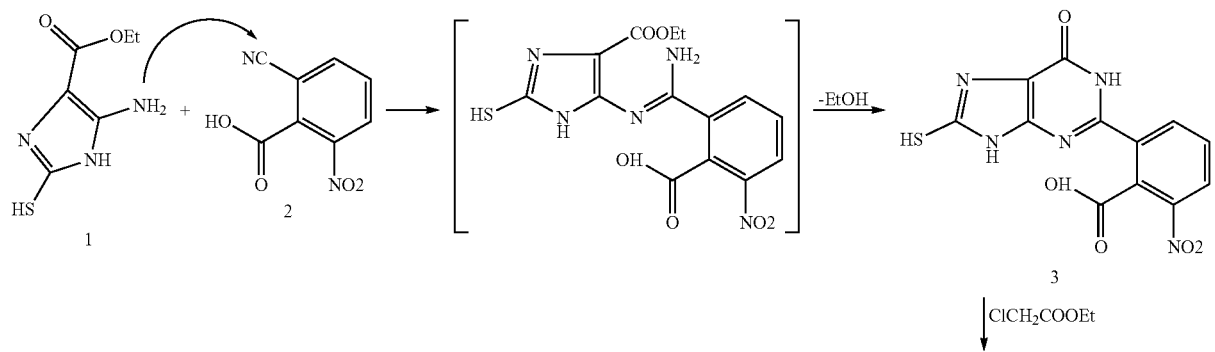

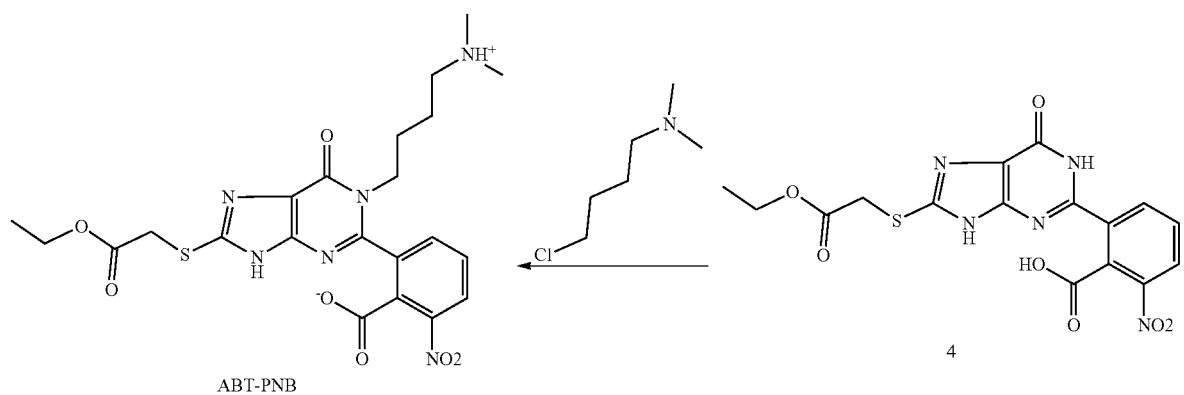

ABT-PNB

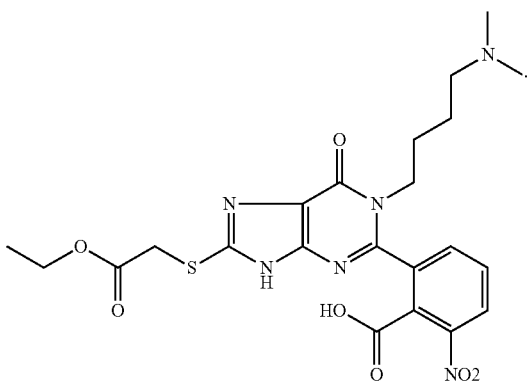

In certain embodiments, the nitrogen-based fertilizer in the core of the present compositions is urea.

In a further embodiment, the at least one coating layer of the present compositions comprises multiple coating layers. In this regard, the multiple coating layers can comprise two, three, four, or more coating layers. In certain embodiments, each of the potassium compound, chitosan, and 2-(1-(4-(dimethylamino)butyl)-8-((2-ethoxy-2-oxoethyl)thio)-6-oxo-6,9-dihydro-1H-purin-2-yl)-6-nitrobenzoic acid can be in a separate coating layer of the multiple coating layers. In other embodiments, each of the potassium compound, chitosan, and 2-(1-(4-(dimethylamino)butyl)-8-((2-ethoxy-2-oxoethyl)thio)-6-oxo-6,9-dihydro-1H-purin-2-yl)-6-nitrobenzoic acid can be in a single coating layer of the at least one coating layer.

In an embodiment, the potassium compound used herein can be selected from the group consisting of potassium phosphate, potassium nitrate, potassium tartrate, and combinations thereof.

In further embodiments, the at least one coating layer can comprise about 1% to about 20% by weight, about 1% to about 15% by weight, about 1% by weight, about 2% by weight, about 3% by weight, about 4% by weight, about 5% by weight, about 6% by weight, about 7% by weight, about 8% by weight, about 9% by weight, about 10% by weight, about 11% by weight, about 12% by weight, about 13% by weight, about 14% by weight, about 15% by weight, about 16% by weight, about 1% by weight, about 18% by weight, about 19% by weight, or about 20% by weight, of the potassium compound.

The at least one coating layer can further comprise about 2% to about 8% by weight, about 2% by weight, about 3% by weight, about 4% by weight, about 5% by weight, about 6% by weight, about 7% by weight, or about % by weight of chitosan, and about 1% to about 10% by weight, about 1% to about 5% by weight, about 1% by weight, about 2% by weight, about 3% by weight, about 4% by weight, about 5% by weight, about 6% by weight, about 7% by weight, about 8% by weight, about 9% by weight, or about 10% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid.

In another embodiment, the core can comprise about 0.25 to about 3 L/tonne, about 0.5 to about 2 L/tonne, about 1 to about 1.5 L/tonne, about 0.5 L/tonne, about 1 L/tonne, about 1.5 L/tonne, about 2 L/tonne, about 2.5 L/tonne, or about 3 L/tonne of urea.

In this regard, in one embodiment of the present subject matter, the at least one coating layer comprises about 10% by weight of potassium phosphate, about 5% by weight of chitosan, and about 2% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid, and the core comprises about 2 L/tonne of urea.

In another embodiment of the present subject matter, the at least one coating layer comprises about 10% by weight of potassium phosphate, about 5% by weight of chitosan, and about 3% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid, and the core comprises about 1 to about 1.5 L/tonne of urea.

In a further embodiment of the present subject matter, the at least one coating layer comprises about 15% by weight of potassium nitrate, about 5% by weight of chitosan, and about 1% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid, and the core comprises about 2 L/tonne of urea.

In still another embodiment of the present subject matter, the at least one coating layer comprises about 3% by weight of potassium tartrate, about 5% by weight of chitosan, and about 4% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid, and the core comprises about 0.5 L/tonne of urea.

In still yet another embodiment of the present subject matter, the at least one coating layer comprises about 1% by weight of potassium tartrate, about 5% by weight of chitosan, and about 5% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid, and the core comprises about 0.5 L/tonne of urea.

In this regard, Table 1 describes certain specific, non-limiting exemplary embodiments of the various NASF1 compositions described herein, and certain of their respective distinctive features and advantages.

TABLE 1

| NASF1A | NASF1B | NASF1C | NASF1D | NASF1E |
|---|---|---|---|---|
| 2% ABT-PNB | 3% ABT-PNB | 1% ABT-PNB | 4% ABT-PNB | 5% ABT-PNB |
| 10% Potassium phosphate | 10% Potassium phosphate | 15% potassium nitrate | 3% potassium tartarate | 1% potassium tartarate |
| 5% Chitosan | 5% Chitosan | 5% Chitosan | 5% Chitosan | 5% Chitosan |
| 2 L/Tonne urea | 1-1.5 L/Tonne urea | 2 L/Tonne urea | 0.5 L/Tonne urea | 0.5 L/Toone urea |
| Inhibit NH$_3$ volatilization | Inhibit NH$_3$ volatilization and nitrification | Inhibit NH$_3$ volatilization | Inhibit NH$_3$ volatilization | Inhibit NH$_3$ volatilization |

TABLE 1-continued

| NASF1A | NASF1B | NASF1C | NASF1D | NASF1E |
|---|---|---|---|---|
| Use in warmer environment | Use in warmer environment with high moisture | Use in colder environment | Use in colder environment | Use in colder environment |
| Effective 1-1.5 months | Effective 1-2 months | Effective 2 months | Effective 1 months | Effective 40 days |

In an embodiment, in use, the at least one coating layer permits water to penetrate the composition to contact the fertilizer to produce a fertilizer solution and permits the fertilizer solution to exit the composition and treat crops to which the composition is applied.

In certain embodiments, the compositions described herein can be formulated as a hydrogel. In further embodiments, the core comprising the nitrogen-based fertilizer of the compositions described herein can be a nitrogen fixed carbon dot.

The NASF1 product as described herein may be used in irrigation of agricultural soil lands at appropriate cost, and can reduce fertilizer usage to encourage and help farmers. Since the coated nitrogen fertilizer particles provide nitrogen to the plant roots gradually (slow release), the loss of nitrates and nitrites in ground water are reduced. This keeps the soil environment clean. Also, reduction of the nitrogen gas volatilization can reduce air pollution. Furthermore, the addition of coated nitrogen fertilizer granules in saline soil can increase the nitrogen use efficiency by reducing the transformation of nitrogen into a form unavailable for plants to use.

The presently disclosed subject matter relates to a nitrogen activator additive (NASF1) to stabilize nitrogen fertilizer, where the activator is coated onto the fertilizer to reduce the use and release of and protect the nitrogen fertilizer, an NASF1 activator-coated particle, as well as processes for synthesizing and using said nitrogen activator additive (NASF1).

In an embodiment, the present subject matter relates to a method for synthesizing the present compositions. In this regard, one embodiment of such synthesis methods involves first forming the urea-containing core in the form of nitrogen fixed carbon dots (N-CDs) via a hydrothermal method as described by Rahmani et al., "One-step hydrothermal-assisted synthesis of highly fluorescent N-doped carbon dots from gum tragacanth: Luminescent stability and sensitive probe for Au3+ ions", Opt Mater 2019: 97:109356. Doi.10.1016/j.optmat.2019.109356, the contents of which are hereby incorporated by reference in their entirety.

For example, 1 mmole of chitosan can be dissolved in an appropriate solvent such as, by way of non-limiting example, ethylene diamine. The resultant mixture can then be transferred to an autoclave containing 1 mmole nano urea, followed by heating to a temperature of about 150° C. to about 200° C., or about 180° C., for several hours, for example, 10 hours. The obtained solution can then be centrifuged to remove any solid deposits. The resultant supernatant solution of N-CDs can then be separated, with the N-CDs solid product obtained by freeze-drying.

The present compositions, in the form of a nanogel, can then be obtained by a one-pot free radical graft copolymerization of the N-CDs with an acrylate on an aqueous dispersion of the N-CDs using ammonium persulfate (APS) as an initiator.

For the coating layer(s), the desired amount of chitosan can be dissolved in an appropriate solvent including, by way of non-limiting example, acetic acid to form a homogenous solution. Desired amounts of acrylamide and/or sodium acrylate monomers can then be added to the homogenous solution, followed by the desired amount of the ABT-PNB. A crosslinker such as, by way of non-limiting example, methylenebisacrylamide, can also be added. Desired volumes of the N-CDs and the desired potassium compound can then be added to the solution, as can tetramethylethylenediamine to serve as a catalyst. Vigorous stirring and ultrasonic polymerization, along with a further addition of APS as an initiator, can then be employed. This results in a nanogel composition of the present subject matter.

The nanogel composition can be further processed by washing one or more times with an ethanol/water mixture, followed by drying to obtain the final NASF1 product. The NASF1 can be isolated from any hydrolysates by precipitation of acidified hydrolysate. For example, the hydrolysate can be acidified to a pH of about 5.5. This can result in NASF1 pellets, which can be filtered, washed with ethanol, air dried to evaporate any excess ethanol, precipitated at a pH of about 1.5, and then washed with an acidified solution having a pH of about 2.0 before freeze drying. An example of the resultant pellets can be seen by referring to FIG. 1.

In an embodiment, present subject matter relates to a method for using the NASF1 additive-coated fertilizer for agricultural crop improvements. In this regard, the present subject matter relates to a method of fertilizing crops, comprising applying the compositions as described herein to said crops. By practicing these methods, 1 kg of the coated slow-release fertilizer composition comprising the urea as the nitrogen-based fertilizer has an equivalent fertilizing effect as 10 kg of an uncoated fertilizer composition comprising urea.

In an embodiment, the crops to which the present compositions can be applied are selected from the group consisting of wheat, corn, olives, palm trees, and any combination thereof. In another embodiment, the crops can be selected from the group consisting of wheat, corn, and combinations thereof. Other crops requiring high amounts of nitrogen may be further fertilized according to the compositions and methods described herein.

In an embodiment, the present methods can be carried out in soil having a low, medium, or high salinity.

Figure 3:
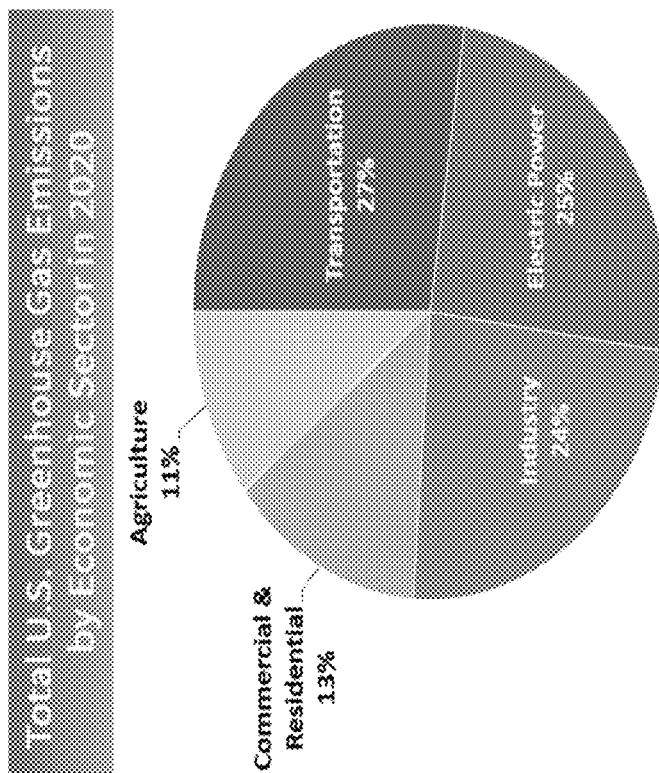
FIG. 3 shows the multiple sources of greenhouse gas (GHG) emissions by economic sector in the U.S. in 2020.

Regarding the reduction of greenhouse gas emissions, it is expected that reducing the amounts of the applied urea in fields of agricultural crops will reduce the nitrogenous gas emissions, hence helping to reduce the hazards of climate change. Additionally, it is well known that agricultural wastes in their raw form are a major source for gas emissions (11% of 2020 greenhouse gas emissions (see FIG. 3), particularly $CO_2$. The agricultural sector is one of the main sectors generating the largest quantities of agricultural waste, which may be allowed to accumulate indiscriminately and constitute a nuisance to global health. The benefits of recycling of agricultural wastes include reduction of greenhouse gas emissions and reduction of the use of fossil fuel, as well as the development of new green markets, creation of jobs, production of bio-energy and bio-conversion of agricultural solid wastes to animal feed. Therefore, transforming and recycling these wastes into beneficial products such as coating materials will assist in reducing greenhouse gas emissions.

Since the coated nitrogen fertilizers particles described herein will provide nitrogen to plant roots gradually (slow release), the loss of nitrates and nitrites in ground water will be reduced. This will keep the soil environment clean and safe. Also, reduction of nitrogen gas volatilization will reduce air pollution. Furthermore, the addition of coated nitrogen fertilizer granules in saline soil will increase the nitrogen use efficiency by reducing the transformation of nitrogen into an unavailable form for plants.

The subject matter of the present application can be further understood by referring to the following examples.

EXAMPLES

Example 1

Synthesis of ABT-PNB: The reactant was reduced rapidly with Ultrasonic-Microwave-UV Synthesis (XH-Beijing 300UL, Xianzhi Technology Limited Co., India). Microwave and ultrasonic parameters in which microwave power was 950 W and the programmed temperature rate was from 20° C. to 150° C. (4 min) with maintenance for 5 min and the intensity of ultrasonic was truncated grade during the entire process. The yield product was washed with alcohol, and then three times centrifuged with water deionized, dried in overnight at 75° C.

Figure 6:
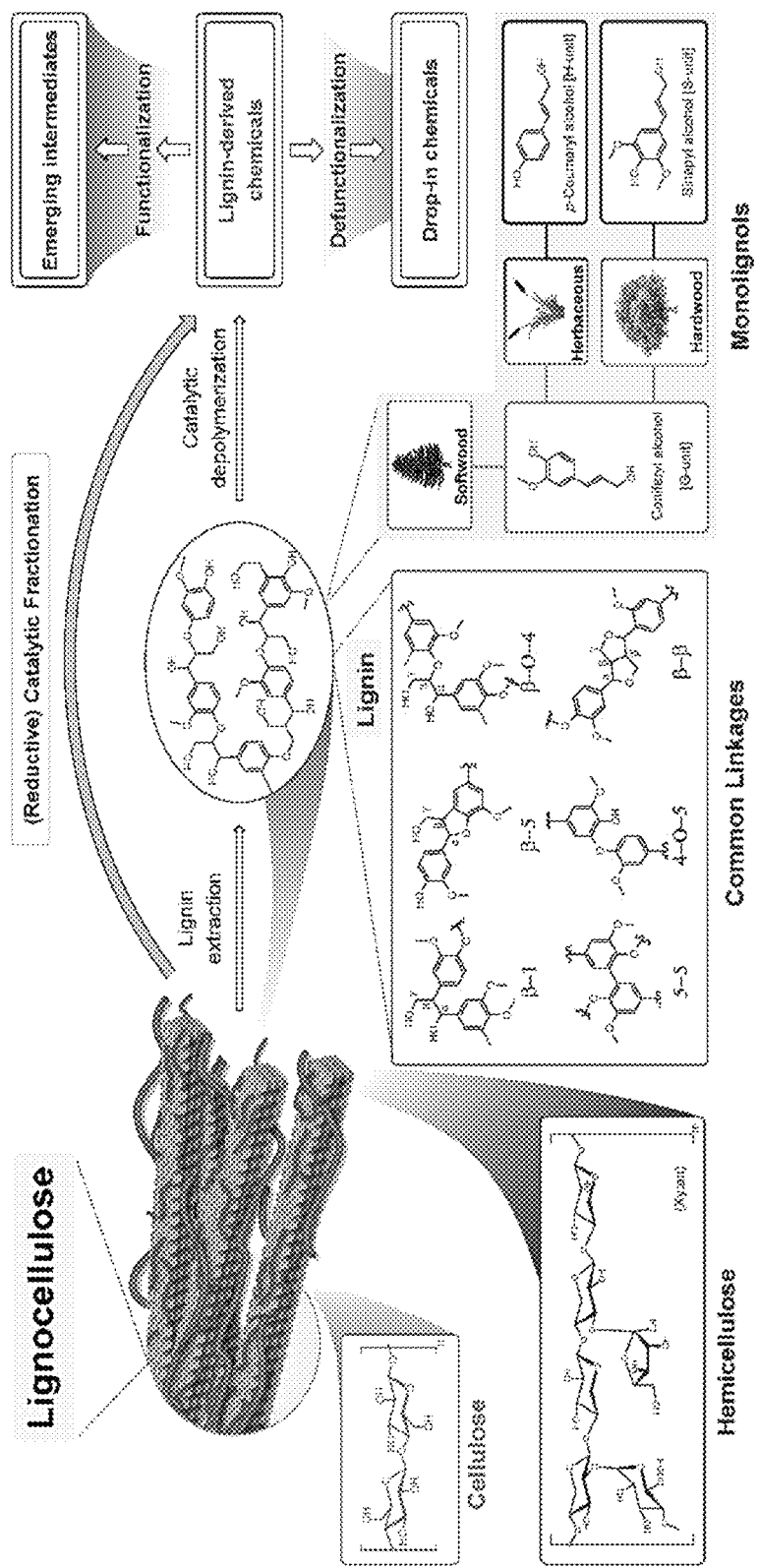
FIG. 6 outlines the important precursors isolated from lignin at MW-US reaction conditions either in the presence or absence of a catalyst.

By changing the MW reduction temperature (200° C. to 140° C.) with MW time (10 min to 5 min) that exploring the influence of ultrasonic-assisted-with microwave synthesis on the performance for lignocellulose and screen out the optimal synthesis condition. The extracted materials can isolate more than 15 compounds depending upon the pressure, temperature, time of the reaction, and nano catalyst used. Computational chemical analysis DFT can help determine the energies favorable to isolate the important precursors as shown in FIG. 6. These precursors can be used and required to synthesize the desired heterocyclic derivatives as antimicrobial, antioxidant, insecticidal and agrochemical products.

Referring to Scheme 2 above, reaction of 0.2 mmol ethyl cyanoacetate with 0.2 mmol thiourea under MW-US condition for 5 min afforded compound 1. One pot reaction of 0.1 mmole of the compound (1) with 0.1 mmole of 2-nitro-6-cyanobenzoic acid (2) in boiling 2 mL ethanol under MW reaction condition for 10 min afforded 6-(imidazo[4,5-d] pyrimidin-2yl) benzoic acid derivative 3. Reflux reaction of the 0.01 mol compound 3 with 0.02 mole ethylchloroacetate in 10 mL acetone for 5 h afforded the ester 4. US promoted reaction of the 0.01 mol of the compound 4 was allowed to react with 0.01 mol of 4-(dimethylamino)butylchloride, thereby affording the desired fertilized ionic liquid ABT-PNB. The final product is considered as a nitrogen activator, it can be stabilized, and it is easily dissolved in water.

Example 2

Synthesis of NASF1: Synthesis of nitrogen fixed carbon dots (N CDs) via hydrothermal method. 1 mmole chitosan was dissolved in 20 mL ethylene diamine and stirred for 20 min. The resulting mixture was transferred into a Teflon-lined autoclave containing 1 mmole nano urea and was heated at 180° C. for 10 h. Then, the obtained dark brownish solution was centrifuged at 20,000 rpm/min twice every 15 min to remove the deposit. The supernatant solution of N-CDs was separated, and the solid product (N-CDs) was obtained by freeze-drying. The product was stored at 4° C. for further use. Microwave synthesis of poly N-CDs hybrid nanogel was conducted via one-pot free radical graft copolymerization with Acrylate on aqueous dispersion N-CDs backbone using APS as an initiator.

Diverse nanogels with required amounts of initial materials were then obtained. A desired amount of chitosan was dissolved in 25 mL of 1 wt % acetic acid solution and stirred at room temperature for 1 h to acquire a homogeneous solution with a 25 mL of distilled water and stirred at 60° C. for 1 h. Then, desired amounts of acrylamide and sodium acrylate monomers were added. Also, various amounts (0.05-0.5 g) of (1-(4-(dimethylamino)butyl)-8-((2-ethoxy-2-oxoethyl)thio)-6-oxo-6,9-dihydro-1H-purin-2-yl)-6-nitrobenzoic acid with (0.5 g) methylenebisacrylamide as a crosslinker was added to the mixture under vigorous stirring.

Then, various volumes of N-CDs aqueous solution (25 mg/L) and 20 mL potassium phosphate (4% wt) were added, as well as 0.1 mL tetramethylethylenediamine as a catalyst was added. A vigorous stirring with ultrasonic polymerization was carried out by the addition of APS (0.01-0.1 g) as an initiator. Lastly, the obtained nanogels were washed several times with water/ethanol and were dried in oven at 80° C.

Example 3

The microwave and ultrasound-assisted synthesized nanogel with the MW-US irradiation was produced by the microwave-sonic system SOMERSET (England, 50 MHz) provided with a horn with an ultimate power of 500 W and sonication time of 0, 10, 20, 25, and 30 min in specific ionic liquid at 90° C. Then, the mixture was continuously stirred at 90° C. for a total period of 1 h. After that, the mixture was washed, filtrated, and dried at 80° C. for 8 h. The NASF1 was isolated from hydrolysates by precipitation of the acidified hydrolysate (pH was adjusted to 5.5) with three volumes of 95% ethanol for 3 h. Synthesis pellets rich NASF1 were filtered, washed with 70% ethanol, and air-dried after the evaporation of ethanol, precipitation at pH 1.5 adjusted, then washed with acidified solution pH 2.0 and freeze-dried.

Example 4

Through pilot experiments conducted on olives in the Siwa region and on palm trees in the New Valley region, it was found that the potential of one-kilogram coated urea to fertilize both crops (olives and palm trees) is equivalent to 10 kg of normal urea (non-coated).

It is to be understood that the compositions, systems, and methods as described herein are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of fertilizing crops, comprising applying a nitrogen activator stabilizer fertilizer (NASF1) composition to said crops; the composition comprising a coated slow-release fertilizer composition comprising:

a core comprising a nitrogen-based fertilizer; and
at least one coating layer surrounding the core, wherein the at least one coating layer comprises a potassium compound, chitosan, and 2-(1-(4-(dimethylamino) butyl)-8-((2-ethoxy-2-oxoethyl)thio)-6-oxo-6,9-dihydro-1H-purin-2-yl)-6-nitrobenzoic acid (ABT-PNB), with the ABT-PNB having the following structure:

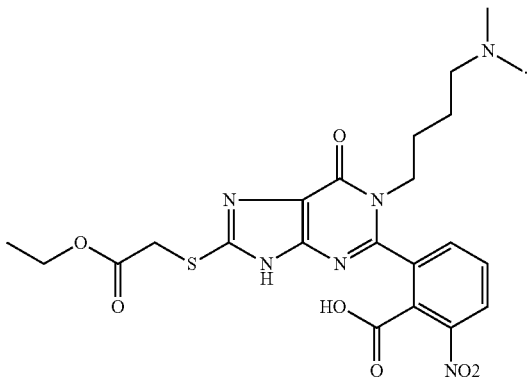

2. The method of claim 1, wherein 1 kg of the coated slow-release fertilizer composition comprising urea as the nitrogen-based fertilizer has an equivalent fertilizing effect as 10 kg of an uncoated fertilizer composition comprising urea.

3. The method of claim 1, wherein the crops are selected from the group consisting of wheat, corn, olives, palm trees, and any combination thereof.

4. The method of claim 1, wherein the nitrogen-based fertilizer is urea.

5. The method of claim 1, wherein the at least one coating layer comprises multiple coating layers.

6. The method of claim 5, wherein the multiple coating layers comprise two, three, or four coating layers.

7. The method of claim 5, wherein each of the potassium compound, chitosan, and 2-(1-(4-(dimethylamino)butyl)-8-((2-ethoxy-2-oxoethyl)thio)-6-oxo-6,9-dihydro-1H-purin-2-yl)-6-nitrobenzoic acid are in a separate coating layer of the multiple coating layers.

8. The method of claim 1, wherein each of the potassium compound, chitosan, and 2-(1-(4-(dimethylamino)butyl)-8-((2-ethoxy-2-oxoethyl)thio)-6-oxo-6,9-dihydro-1H-purin-2-yl)-6-nitrobenzoic acid are in a single coating layer of the at least one coating layer.

9. The method of claim 1, wherein the potassium compound is selected from the group consisting of potassium phosphate, potassium nitrate, potassium tartrate, and combinations thereof.

10. The method of claim 4, wherein the at least one coating layer comprises about 1% to about 20% by weight of the potassium compound, about 2% to about 8% by weight of chitosan, and about 1% to about 10% by weight of 2-(1-(4-(dimethylamino)butyl)-8-((2-ethoxy-2-oxoethyl) thio)-6-oxo-6,9-dihydro-1H-purin-2-yl)-6-nitrobenzoic acid.

11. The method of claim 10, wherein the at least one coating layer comprises about 10% by weight of potassium phosphate, about 5% by weight of chitosan, and about 2% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid.

12. The method of claim 10, wherein the at least one coating layer comprises about 10% by weight of potassium phosphate, about 5% by weight of chitosan, and about 3% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid.

13. The method of claim 10, wherein the at least one coating layer comprises about 15% by weight of potassium nitrate, about 5% by weight of chitosan, and about 1% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid.

14. The method of claim 10, wherein the at least one coating layer comprises about 3% by weight of potassium tartrate, about 5% by weight of chitosan, and about 4% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid.

15. The method of claim 10, wherein the at least one coating layer comprises about 1% by weight of potassium tartrate, about 5% by weight of chitosan, and about 5% by weight of 2-(1-(4-(dimethylamino)butyl)-8-((2-ethoxy-2-oxoethyl)thio)-6-oxo-6,9-dihydro-1H-purin-2-yl)-6-nitrobenzoic acid.

16. The method of claim 1, wherein the at least on coating layer permits water to penetrate the composition to contact the fertilizer to produce a fertilizer solution and permits the fertilizer solution to exit the composition and treat crops to which the composition is applied.

17. The method of claim 1, wherein the composition is a hydrogel.

18. The method of claim 1, wherein the core comprising the nitrogen-based fertilizer is a nitrogen fixed carbon dot.

* * * * *